United States Patent
Kaye et al.

(10) Patent No.: US 9,144,373 B2
(45) Date of Patent: Sep. 29, 2015

(54) WATER BOTTLE ADAPTER FOR COUPLING AN ENDOSCOPE TO A WATER BOTTLE

(75) Inventors: Christopher J. Kaye, Concord, OH (US); Alison Streiff, Painesville, OH (US); Gary E. Mann, Mentor, OH (US)

(73) Assignee: United States Endoscopy Group, Inc., Mentor, OH (US)

( * ) Notice: Subject to any disclaimer, the term of this patent is extended or adjusted under 35 U.S.C. 154(b) by 267 days.

(21) Appl. No.: 13/093,989

(22) Filed: Apr. 26, 2011

(65) Prior Publication Data

US 2011/0263939 A1    Oct. 27, 2011

Related U.S. Application Data

(60) Provisional application No. 61/327,997, filed on Apr. 26, 2010.

(51) Int. Cl.
*A61B 1/12* (2006.01)
*A61B 1/00* (2006.01)

(52) U.S. Cl.
CPC .............. *A61B 1/121* (2013.01); *A61B 1/00128* (2013.01)

(58) Field of Classification Search
USPC .................................. 600/132–133, 153–159
See application file for complete search history.

(56) References Cited

U.S. PATENT DOCUMENTS

| | | | |
|---|---|---|---|
| 2,186,908 A | 1/1940 | Page et al. | |
| 4,519,385 A * | 5/1985 | Atkinson et al. | 601/161 |
| 4,552,130 A * | 11/1985 | Kinoshita | 600/158 |
| 4,760,838 A * | 8/1988 | Fukuda | 600/158 |
| 4,997,429 A * | 3/1991 | Dickerhoff et al. | 604/411 |
| 5,133,336 A | 7/1992 | Savitt et al. | |
| 5,176,629 A | 1/1993 | Kullas et al. | |
| 5,297,537 A | 3/1994 | Savitt et al. | |
| 5,333,603 A * | 8/1994 | Schuman | 600/158 |
| 5,437,654 A * | 8/1995 | McVay | 604/403 |
| 5,505,707 A | 4/1996 | Manzie et al. | |

(Continued)

FOREIGN PATENT DOCUMENTS

WO    2004/023987    3/2004

OTHER PUBLICATIONS

Weng et al., "Fundamentals and Material Development for Thermoplastic Elastomer (TPE) Overmolding", in Journal of Injection Molding Technology, vol. 4, No. 1, Mar. 2000.

(Continued)

*Primary Examiner* — Matthew J Kasztejna
(74) *Attorney, Agent, or Firm* — Calfee, Halter & Griswold LLP

(57) ABSTRACT

An adapter for coupling a disposable water bottle to an endoscope including a cap manufactured from a thermoplastic elastomer material. The cap is removably secured to an associated water bottle. The cap includes a first port and a second port. The adapter further includes a scope connector manufactured from the thermoplastic elastomer and/or thermoset elastomer having a first scope connector port and second scope connector port, wherein the scope connector is configured to be frictionally coupled to an endoscope. A first supply tube couples to the first port of the cap and the first scope connector port and a second supply tube coupled to the second port of the cap and the second scope connector port. By using a thermoplastic elastomer and/or thermoset elastomer material, a simplified adapter is provided, which substantially reduces design and manufacturing costs.

21 Claims, 3 Drawing Sheets

(56) References Cited

U.S. PATENT DOCUMENTS

| | | | |
|---|---|---|---|
| 5,755,360 A | 5/1998 | Elliott | |
| 5,782,383 A | 7/1998 | Robinson | |
| 5,830,128 A | 11/1998 | Tanaka | |
| 6,210,322 B1 | 4/2001 | Byrne | |
| 6,481,589 B2 | 11/2002 | Blomdahl et al. | |
| 6,485,412 B1 | 11/2002 | Byrne | |
| 6,702,738 B2 | 3/2004 | Ito | |
| 6,764,442 B2 | 7/2004 | Ota et al. | |
| 6,837,400 B2 * | 1/2005 | Leoncavallo et al. | 222/189.09 |
| 6,881,188 B2 | 4/2005 | Furuya et al. | |
| 8,343,041 B2 | 1/2013 | Byers et al. | |
| 2002/0092858 A1 * | 7/2002 | Bowman | 220/709 |
| 2003/0189023 A1 | 10/2003 | Gonzalez | |
| 2007/0043262 A1 | 2/2007 | Levy et al. | |
| 2008/0072970 A1 | 3/2008 | Gasser et al. | |
| 2008/0132763 A1 | 6/2008 | Isaacson | |
| 2009/0264705 A1 | 10/2009 | Cushner et al. | |
| 2009/0298129 A1 | 12/2009 | Spence et al. | |
| 2010/0237070 A1 | 9/2010 | Coonce et al. | |
| 2012/0277536 A1 | 11/2012 | Kaye et al. | |

OTHER PUBLICATIONS

Office action from U.S. Appl. No. 13/464,263 dated Mar. 11, 2014.
Office Action in U.S. Appl. No. 14/456,783 dated Mar. 19, 2015.

* cited by examiner

WATER BOTTLE ADAPTER FOR COUPLING AN ENDOSCOPE TO A WATER BOTTLE

RELATED APPLICATIONS

This application claims the benefit of U.S. Provisional Application No. 61/327,997 filed Apr. 26, 2010, which is hereby incorporated herein by reference.

TECHNICAL FIELD

The present disclosure relates to endoscope systems. More particularly, the present disclosure relates to an adapter for a disposable water bottle, wherein the adapter is operative for coupling the water bottle to an endoscope system in order to deliver sterilized water to the endoscope instrument.

BACKGROUND

Endoscopic instruments have been developed to provide surgeons with an internal view of the organ or body passage requiring treatment. Such endoscopes typically have channels through which a miniaturized forceps or other device, commonly called flexible instruments, are inserted and advanced. The endoscope assembly includes an elongated flexible cable equipped at one end with an eyepiece or other viewing mechanism and at the other end with an optical head. Only the head is directly and externally connected to the instrument. The cable transmits images or image-producing signals from the illuminated operative site to the viewing mechanism so that the surgeon will have visual confirmation of the action of the instrument's working end.

The cable also provides a flow passage for the delivery of fluid (liquid or gas) for irrigation or other purposes. In conventional practice, it is necessary to provide the optic head with a flow of sterile water. The passage of the sterile water across the optic head prevents the buildup of materials on the optic head.

A conventional endoscope includes a plurality of connectors that can suitably receive various fittings. For example, the connector can include a connector orifice that receives an air inlet and a water inlet. As such, the air and water are delivered through the connector to optic head of the endoscope.

Unfortunately, there is usually great expense associated with the delivery of such sterile water to the endoscope. In past practice, the sterile water has been provided from a water bottle that is directly connected to a tube. The tube generally will have a fitting at one end so as to allow the tube to be connected to the air/water inlet of the endoscope connector. Typically, the fitting will include an inner tube and an outer tube. The outer tube extends into the water bottle. The outer tube is connected to the cap of the water bottle. In normal practice, air is delivered through the area between the inner tube and the outer tube so as to pressurize the interior of the water container. This will force water to flow through the tube and into the endoscope at a desired rate.

After usage, the water bottle, the tubing, and the associated fittings are sterilized. This creates a considerable wasteful expense to the hospital. If the water bottle is sterilized, there is a considerable labor expense associated with the autoclaving of the bottle. There is also the possibility of residual contaminants residing in the area of connection between the tubes and the bottle.

SUMMARY OF INVENTION

Conventional adapters for coupling a water bottle to the endoscopic assembly are made of hard, non-pliable materials that rely on multiple structural components to maintain a suitable seal. As a result, manufacturers are required to take elaborate steps in the manufacturing process to ensure a suitable seal between the air and fluid passage from the water bottle to the endoscope assembly. These additional steps include, for example, requiring ultrasonic welding of small components together, designing complex connecting structures, which are usually implemented with a gasket (or O-ring) to ensure a suitable seal, and the like. With conventional adapters, these additional steps were required to ensure an adequate seal. However, the additional steps are extremely costly and provide no additional value to the customer.

One aspect of the disclosure relates to an adapter for coupling a disposable water bottle to an endoscope including: a cap manufactured from a thermoplastic elastomer and/or an thermoset elastomer, wherein the cap includes an interior surface of the cap, which may include threads or may be formed without threads, for removably securing the cap to an associated water bottle and the cap includes a first port and a second port; a scope connector manufactured from the thermoplastic elastomer and/or the thermoset elastomer having a first scope connector port and second scope connector port, wherein the scope connector is configured to be frictionally coupled to an endoscope; a first supply tube coupled to the first port of the cap and the first scope connector port; and a second supply tube coupled to the second port of the cap and the second scope connector port.

Another aspect of the disclosure relating to an adapter for coupling a disposable water bottle to an endoscope including: a cap manufactured from a thermoplastic elastomer and/or a thermoset elastomer, wherein the cap includes an interior surface of the cap for removably securing the cap to an associated water bottle based on a material interface between the interior surface of the cap and the water bottle, and the cap includes a first port and a second port; a scope connector manufactured from the thermoplastic elastomer and/or a thermoset elastomer having a first scope connector port and second scope connector port, wherein the scope connector is configured to be frictionally coupled to an endoscope; a first supply tube coupled to the first port of the cap and the first scope connector port; and a second supply tube coupled to the second port of the cap and the second scope connector port.

To the accomplishment of the foregoing and related ends, the disclosure, then, comprises the features hereinafter fully described and particularly pointed out in the claims. The following description and the annexed drawings set forth in detail certain illustrative embodiments of the disclosure. These embodiments are indicative, however, of but a few of the various ways in which the principles of the disclosure may be employed.

DETAILED DESCRIPTION

Figure 1:
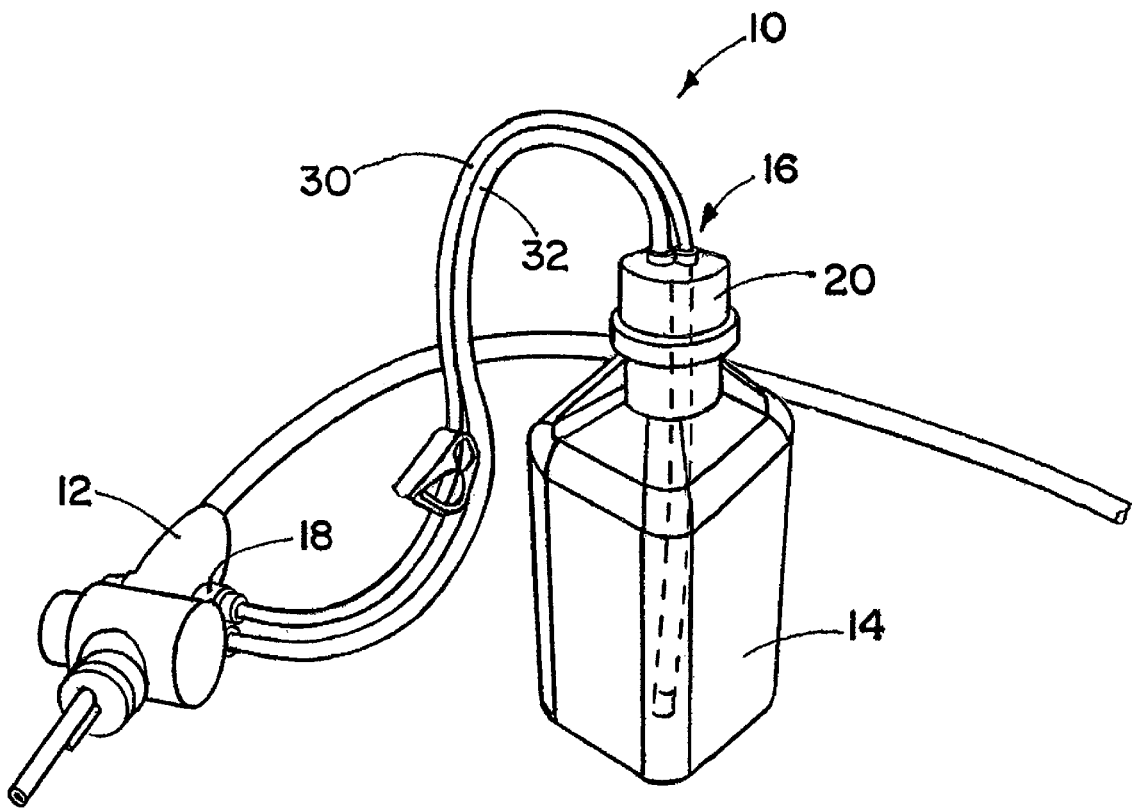
FIG. 1 is an environmental view of an exemplary endoscopic irrigation system.

Embodiments will now be described with reference to the drawings, wherein like reference numerals are used to refer to like elements throughout. It will be understood that the figures are not necessarily to scale.

Aspects of the present disclosure relate to an adapter for coupling a disposable water bottle to an endoscope. As discussed below, the adapter includes a cap for connecting the adapter to a water bottle and a scope connector for coupling the adapter to the endoscope. The adapter includes an air tube and a water tube coupled to air and water ports located on the water bottle cap and the scope connector, respectively. In operation, air forced through the air tube from the endoscope into the water bottle causes water to flow from the water tube into the endoscope assembly field. The water bottle cap and the scope connector are made from a thermoplastic elastomer (TPE) and/or a thermoset elastomer that have sufficient pliability and/or are capable of frictionally engaging with other structures (e.g., endoscope port, air tube, water tube, etc.) in such a manner to provide a substantially air tight seal and at the same time allow a user to easily install and remove the adapter.

Referring to FIG. 1, an exemplary system 10 in accordance with aspects of the present disclosure is illustrated. The system 10 includes an endoscope 12 coupled to a water bottle 14 through an adapter, identified generally in FIG. 1 as reference numeral 16. The adapter 16 is illustrated in additional detail in FIG. 2.

The endoscope 12 may be any type of endoscope that is manufactured by any manufacturer. Preferably, the endoscope is operative to receive dual tubes (e.g., one for air and one for water) at an endoscope connector 18.

The water bottle 14 may be any size and/or type of water bottle. The water bottle 14 may be, for example, a one liter water bottle of a conventional type used in hospitals. The water bottle 14 is conventionally filled with sterile water. It is necessary to use sterile water since the water will pass to the interior of the human body during the process of cleaning the optic head of the endoscopic instrument. The water bottle 14 generally has an externally threaded neck. In normal use, a cap is threadedly secured to the threaded neck, so as to prevent leakage or dispensing of the water from the interior of the bottle during transportation and storage of the water bottle.

Figure 2:
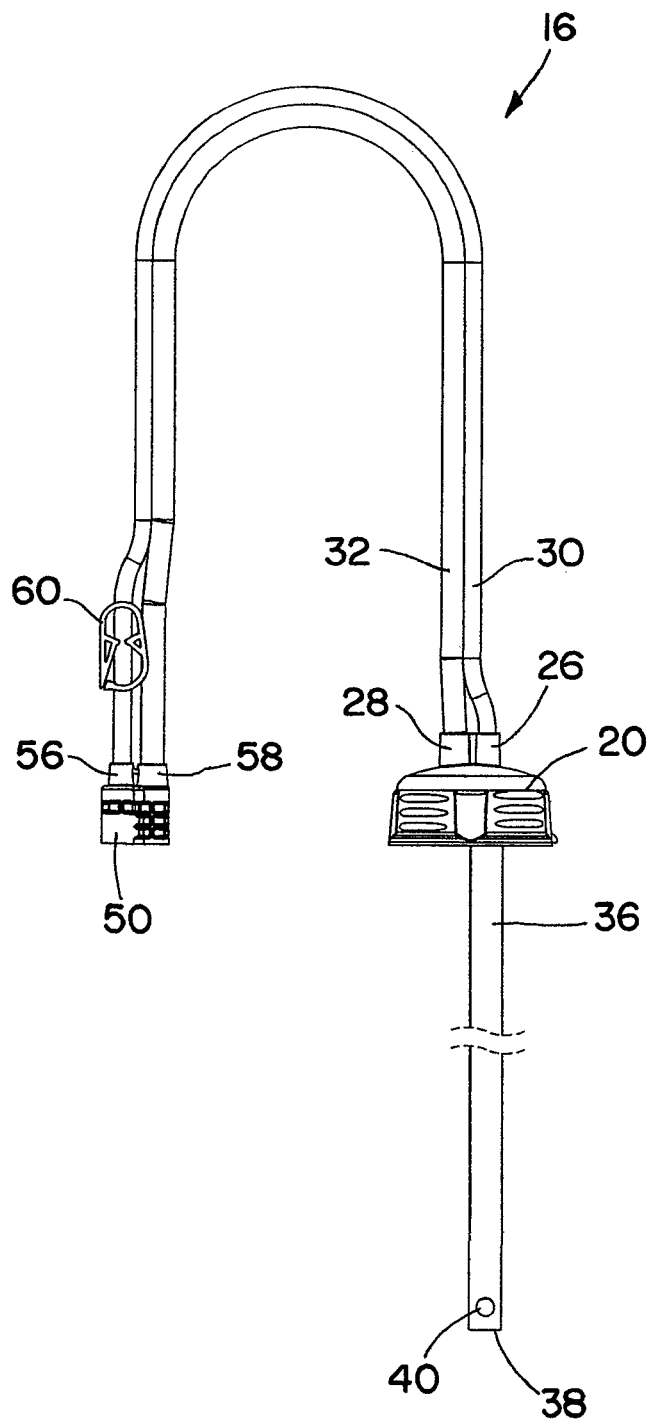
FIG. 2 is a side perspective view of an exemplary adapter.
Figure 3:
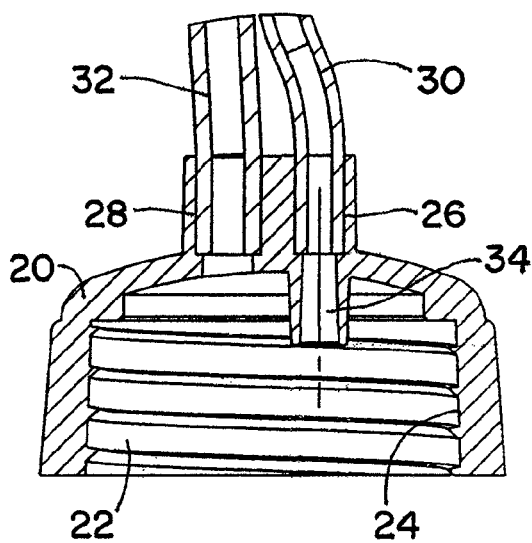
FIG. 3 is a cross-sectional view of an exemplary cap.

In order to affect the use of the adapter 16, it is necessary for the water bottle cap to be threadedly removed from the exterior of the neck of water bottle 14. Adapter 16 may then be secured to the water bottle 14. Referring to FIG. 2, the adapter 16 includes a cap 20. As discussed below, the cap 20 may be formed with one or more threads or without threads. In one embodiment, the cap 20 may include one or more threads 22 on an interior surface 24 of the cap for removably securing the cap to the water bottle 14, as shown in FIG. 3. The interior threads 22 of the cap may be sized to fit over various shapes and sizes of exterior threads that may exist on the neck of the water bottle 14 or the threads 22 may be designed especially to mate with one type of water bottle thread type.

In one embodiment, the threads 22 may be designed so as to match the variation in threads between the various brands of water bottle. In another embodiment, the threads 22 may be buttress threads having a four milliliter pitch (the distance between the threads). As such, even though the thread designs of the various brands of water bottles are different, the particular pitch and shape of the threads 22 are configured so as to allow the cap 20 to be attached to more than one type of water bottle.

Figure 4:
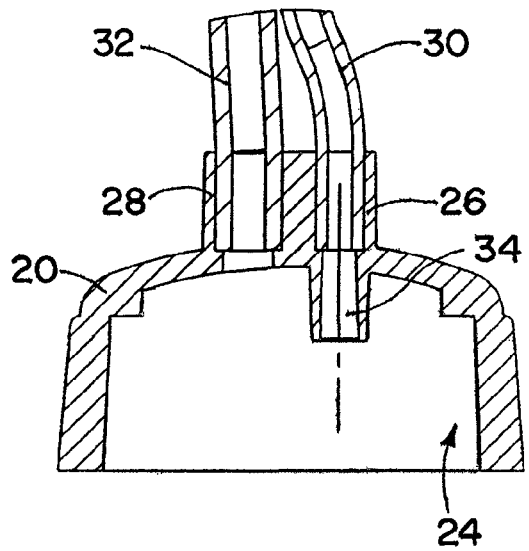
FIG. 4 is a cross-sectional view on another exemplary cap.

In another embodiment, the cap 20 may be formed without threads, as illustrated in FIG. 4. The cap 20 includes an interior surface for removably securing the cap to the water bottle 14 (e.g., an outside diameter of the water bottle opening). The cap is secured to the bottle based on the ability of the elastomeric material to be compliant and conform to the outside bottle diameter in order to form a seal. For example, the cap 20 may stretched or otherwise temporarily enlarged to fit over the water bottle 14. When the stretching or enlarging force is released, the cap will frictionally engage with the water bottle. In such embodiment, the cap 20 may take any desirable size and shape, so long as the interior surface of the cap is capable forming a suitable interface with the water bottle.

In contrast to many prior art water bottle caps that rely on gaskets or a series of complicated connection structures to establish an air and water tight seal with the water bottle, the cap 20 is manufactured from a thermoplastic elastomer (TPE) and/or a thermoset elastomer that establishes an air water tight seal with the water bottle 14, without relying on any additional sealing mechanism. Exemplary materials that may be used in accordance with aspects of the present disclosure include: styrenic block copolymers, polyolefin blends, elastomeric alloys (TPE-v or TPV), thermoplastic polyurethanes, thermoplastic copolyester and/or thermoplastic polyamides, silicone, natural and synthetic rubbers, and equivalents. Examples of products that come from block copolymers group are Styroflex (BASF), Kraton (Shell chemicals), Pellethane (Dow Chemical), Pebax, Arnitel (DSM), Hytrel (Du Pont) and more. While there are now many commercial products of elastomer alloy, these include: Dryflex ([VTC TPE Group]), Santoprene (Monsanto Company), Geolast (Monsanto), Sarlink (DSM), Forprene (So.F.Ter. S.p.a.), Alcryn (Du Pont) and Evoprene ([AlphaGary]). In one embodiment, the cap 20 may be made of flexible polyvinyl chloride (PVC), for example. One of ordinary skill in the art will appreciate that the above list is illustrative and not intended to limit the scope of the present disclosure.

The cap 20 includes a first port 26 and a second port 28 for introduction of water and air (or other gas) into the bottle 14 though the cap 20, as illustrated in FIGS. 2-4. The first port 26 and the second port 28 extend generally from an outer surface of the cap and are formed through the cap 20 in order to provide pathways for water and/or air to enter and/or exit the ports. In actual use, a controlled flow of air is maintained through the second port 28 so as to control the flow of water through the interior first port 26. If more water flow is desired, then greater air pressure is delivered through the second port 28 to the interior of the water bottle 14. If less water flow is desired, then less air pressure is applied.

The first port 26 and the second port 28 can be formed integrally with the cap 20. A first supply tube 30 may be coupled to the first port 26. A second supply tube 32 is coupled to the second port 28. The supply tubes 30, 32 may be secured to the respective ports in any desirable manner. In one embodiment, the supply tubes may be secured to the respective port during formation of the cap 20 and ports 26, 28, for example, in an over-molding manufacturing process. In such a process, the supply tubes 30, 32 may be placed in a mold that forms the cap 20, along with the first and second ports 26, 28. When the molding process is completed (e.g., using an injection molding process, etc.), the first supply tube 30 is secured to the first port 26 and the second supply tube 32 is secured to the second port 28 during formation of the cap with first and second ports.

In another embodiment, the supply tubes 30, 32 may be secured to the first and second ports 26, 28 after formation of the ports. In such case, an adhesive may be used to secure the first supply tube 30 to the first port 26 and the second supply tube 32 to the second port 28. An exemplary adhesive may be, for example, cyanocrylate (CA), which may be supplied by Loctite, Dymax, for example.

The cap 20 may also include a third port 34, which is illustrated in FIGS. 3 and 4. The third port 34 can be fluidly connected to the first port 26, such that fluid may flow from third port 34 through the first port 26. As illustrated in FIG. 2, a water bottle supply tube 36 may be secured to the third port 34 by an adhesive and/or any other desirable mechanism. In use, the water bottle supply tube 36 may be inserted through the neck of the water bottle 14. As the cap 20 is threadedly secured to the water bottle 14, the water bottle supply tube 36 is lowered into the water bottle 14. The water bottle supply tube 36 may have an end 38 that rests at or near the bottom of the water bottle 14 in order to draw water from the water bottle 14. In one embodiment, the water bottle supply tube 36 has one or more voids 40 formed near the end 38 for facilitating the drawing of water from the water bottle 14. In another embodiment, an anchor (not shown) may be affixed to the water bottle supply tube 36 so as to ensure the end 38 remains at or near the bottom of the water bottle 14.

Another embodiment of the present disclosure is directed to the first supply tube 30 terminating at or near the bottom of the water bottle 14. In such an embodiment, the third port 34 disclosed may not be needed, as such the third port 34 is optional.

The first and second supply tubes 30, 32 may have one end that is secured within the first and second ports 26, 28, as illustrated in FIGS. 3 and 4. In another embodiment, the ends of the first and second supply tubes 30, 32 may extend past the first and second ports 26, 28.

Figure 5:
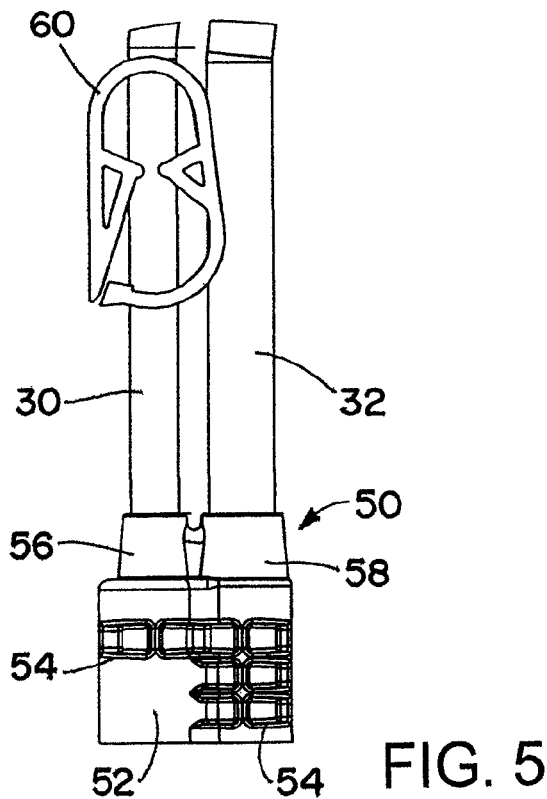
FIG. 5 is a side perspective view of an exemplary scope connector.
Figure 6:
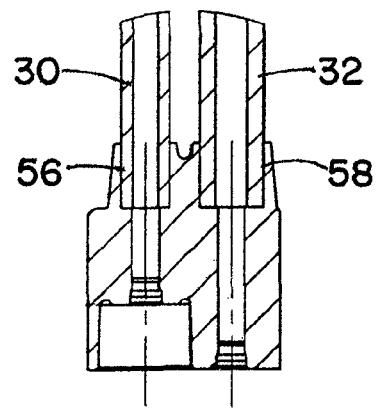
FIG. 6 is a cross-sectional view of the exemplary scope connector.

The adapter 16 further includes a scope connector 50, as illustrated in FIGS. 5 and 6. The scope connector 50 generally has an outer housing 52 that is configured to mate with endoscope connector 18. As shown in FIG. 5, the scope connector 50 is formed to be matingly inserted into the endoscope connector 18. In order to enhance the seal of the scope connector 50 within the endoscope connector 18, the scope connector 50 may include one or more ridges 54 formed in the housing 52. The one or more ridges 54 may be of varying size. The housing 52 and one or more ridges 54 are sized to provide an air and water tight seal with the endoscope connector 18. In particular, the housing 52 of the scope connector is configured and size to frictionally engage with the endoscope connector 18 in such a manner to form an air tight seal.

Like the cap 20 discussed above, the scope connector 50 may be manufactured from a thermoplastic elastomer (TPE) and/or thermoset material, such that an air and water tight seal may be formed between the endoscope connector 18 and the scope connector 50 without requiring any additional sealing mechanism (e.g., a gasket, O-ring, etc.). One of ordinary skill in the art will readily appreciate that the cap 20 and the scope connector 50 may be manufactured from the same or different materials.

The scope connector 50 includes a first scope connector port 56 and second scope connector port 58. The ports 56, 58 are coupled to first supply tube 30 and the second supply tube 32, respectively in such a way to establish two independent passageways between the water bottle 14 and the endoscope 12. For example, the first supply tube 30 is coupled to the first port 26 of the cap 20 and the first scope connector port 56. Likewise, the second supply tube 32 is coupled to the second port 28 of the cap 20 and the second scope connector port 58.

In operation, when water is desired at the endoscope operative sight, air may be forced through second scope connector port 58 though the second supply tube 32 through the second port 28 and into the water bottle 14. As air is forced into the water bottle 14, water is drawn through the water bottle supply tube end 38, through the third port 34 into to the first port 26 of the cap 20. From the first port 26, the water travels through the first supply tube 30 to the first scope connector port 56 for use by the endoscope 12.

The supply tubes 30, 32 may be secured to the respective ports 56, 58 in any desirable manner. In one embodiment, the 30, 32 may be secured to the respective port during formation of the port 56, 58, for example, in an over-molding manufacturing process. In such a process, the supply tubes 30, 32 may be placed in a mold that forms the scope connector 50, along with the first and second ports 56, 58. Such that when the mold is completed, the first supply tube 30 is secured to the first port 56 and the second supply tube 32 is secured to the second port 58 during formation of the cap with first and second ports.

In one embodiment, the supply tubes 30, 32 may be secured to the first and second ports 56, 58 through the use of an adhesive, as discussed above with respect to securing the supply tubes 30, 32 to the first and second ports 26, 28 of the cap 20.

Referring to FIG. 6, the first and second supply tubes 30, 32 may have one end that is secured within the first and second ports of the scope connector 56, 58 to facilitate fluidic communication between the endoscope 12 and the adapter 16 with the water bottle 14.

At least one of the supply tubes 30, 32 may include a pinch clamp 60, as illustrated in FIGS. 2 and 5. The pinch clamp 60 may be used by the operator to stop or start the fluid flow through the liquid supply tube (e.g., the first supply tube 30) at any time.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the disclosure. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. An adapter for coupling a disposable water bottle to an endoscope comprising:

a cap manufactured from a thermoplastic elastomeric and/or an thermoset elastomer, the cap having threads on an interior surface of the cap for removably securing the cap to an associated water bottle, a dome shaped top surface and a protruding tip from the top center surface of the dome, a first port extending from a top side of the cap, and a second port extending from a top side of the cap, wherein the first port and the second port each extend an equal distance away from the dome shaped top surface to a common and single top face of the protruding tip;

a scope connector manufactured from a thermoplastic elastomer and/or the thermoset elastomer having a first scope connector port and second scope connector port, wherein the scope connector is configured to be frictionally coupled to an endoscope;

a first supply tube coupled to the first port of the cap and the first scope connector port;

a second supply tube coupled to the second port of the cap and the second scope connector port; and a clamp disposed on the first supply tube and operable between an open position and a closed position to prohibit fluid flow within the first supply tube in a direction toward the cap;

wherein the first supply tube and the second supply tube are spaced apart, each connected to an opposite half of the protruding tip.

2. The adapter of claim 1, wherein the first supply tube is molded to the first port of the cap during formation of the first port and the second supply tube is molded to the second port of cap during formation of the second port.

3. The adapter of claim 1, wherein the first supply tube is configured to be placed at or near a bottom of the associated water bottle when the adapter is secured to the water bottle.

4. The adapter of claim 1, wherein the first supply tube is molded to the first port of the scope connector during formation of the scope connector and the second supply tube is molded to the second scope connector port during formation of the scope connector.

5. The adapter of claim 1, further including a third port formed in the cap, wherein the third port is in communication with the first port.

6. The adapter of claim 5, further including a water supply tube coupled to the third port.

7. The adapter of claim 1, wherein the first port and the second port of the cap are formed integrally with the cap.

8. The adapter of claim 1, wherein the first scope connector port and second scope connector port are formed integrally.

9. The adapter of claim 1, wherein the scope connector includes a housing that is sized to frictionally engage with the endoscope in such a manner to form an air tight seal.

10. The adapter of claim 9, wherein the housing of scope connector includes one or more ridges formed during the manufacturing process of the housing, wherein the one or more ridges frictionally engages with an endoscope connector.

11. The adapter of claim 10, wherein the scope connector forms the air tight seal with the endoscope without requiring a gasket to make the seal.

12. The adapter of claim 1, wherein the thermoplastic elastomer is at least one material selected from the group consisting of:

styrenic block copolymers, polyolefin blends, elastomeric alloys, thermoplastic polyurethanes, thermoplastic copolyester and thermoplastic polyamides.

13. The adapter of claim 1, wherein the adapter is a molded part.

14. The adapter of claim 13, wherein cap and the scope connector are formed during an injection molding process.

15. The adapter of claim 1, wherein the first port is configured to receive a supply of water and the second port is configured to receive a supply of air such that incoming air through the second port forces water out of the first port.

16. The adapter of claim 1, wherein the cap is manufactured from a first material and the scope connector is manufactured from a different material.

17. A method of performing an endoscopic procedure, the method comprising using an endoscope assembly including a water bottle with an adapter according to claim 1.

18. A method of operating an endoscope, the method comprising coupling a water body to an endoscope with an adapter according to claim 1.

19. An adapter comprising:

a cap having threads on an interior surface for coupling to a water bottle, a dome shaped top surface and a protruding tip from the top center surface of the dome, a single top face, a first cap port extending from a top side of the cap, a second cap port extending from a top side of the cap, and a third cap port extending from a bottom side of the cap, wherein the first cap port and the second cap port each extend an equal distance to the single face;

a scope connector having a first connector port and second connector port, wherein the scope connector is configured to be frictionally coupled to an endoscope;

a first tube coupled to the first cap port and the first connector port;

a second tube coupled to the second cap port and the second connector port;

a third tube coupled to the third cap port; and a clamp disposed on the first tube and operable between an open position and a closed position, wherein the clamp in a closed position prohibits fluid flow within the first tube between the first cap port and the first connector port;

wherein the first cap port and the third cap port are arranged to allow fluid communication from the two ports;

wherein the first supply tube and the second supply tube are spaced apart, each connected to an opposite half of the protruding tip.

20. The assembly of claim 19, wherein the cap and the scope connector are each without a gasket.

21. The assembly of claim 19, wherein the third tube defines at least one void near a distal end.

* * * * *